US006284338B1

(12) United States Patent
Bauman et al.

(10) Patent No.: US 6,284,338 B1
(45) Date of Patent: Sep. 4, 2001

(54) INDEX TAB LABEL INSERT SHEETS

(75) Inventors: Bruce D. Bauman, Tustin; Fiona J. Mills, Newport Beach; Russ D. Pollman, Pomona, all of CA (US)

(73) Assignee: Avery Dennison Corporation, Pasadena, CA (US)

( * ) Notice: Subject to any disclaimer, the term of this patent is extended or adjusted under 35 U.S.C. 154(b) by 0 days.

(21) Appl. No.: 09/178,230

(22) Filed: Oct. 23, 1998

(51) Int. Cl.[7] .............................. A61F 13/02; B32B 7/12

(52) U.S. Cl. ...................... 428/42.3; 428/42.1; 428/42.2; 428/43; 428/354; 40/641

(58) Field of Search ................................ 428/42.3, 42.2, 428/42.1, 354; 40/641, 299, 359, 360; 283/81

(56) References Cited

U.S. PATENT DOCUMENTS

| | | | | |
|---|---|---|---|---|
| 4,558,888 | | 12/1985 | Hanson et al. | 281/23 |
| 4,876,131 | | 10/1989 | Ashby et al. | 428/42 |
| 4,910,058 | | 3/1990 | Jameson | 428/42 |
| 4,952,433 | * | 8/1990 | Tezuka et al. | 428/42 |
| 4,972,615 | * | 11/1990 | Grant | 40/641 |
| 4,983,438 | | 1/1991 | Jameson | 428/42 |
| 5,091,239 | | 2/1992 | Przeworski et al. | 428/195 |
| 5,135,261 | | 8/1992 | Cusack et al. | 285/81 |
| 5,182,152 | * | 1/1993 | Ericson | 428/42 |
| 5,227,209 | | 7/1993 | Garland | 428/40 |
| 5,279,875 | * | 1/1994 | Juszak et al. | 428/42.3 |
| 5,282,649 | | 2/1994 | Williams et al. | 283/56 |
| 5,284,689 | | 2/1994 | Laurash et al. | 428/40 |
| 5,324,078 | | 6/1994 | Bane | 283/81 |
| 5,340,158 | | 8/1994 | Bartl | 283/81 |
| 5,389,415 | | 2/1995 | Kaufmann | 428/40 |
| 5,468,085 | | 11/1995 | Kline | 402/79 |
| 5,486,021 | | 1/1996 | Laurash | 283/81 |
| 5,503,435 | * | 4/1996 | Kline | 283/67 |
| 5,547,227 | | 8/1996 | Laurash et al. | 283/81 |
| 5,651,852 | | 7/1997 | Mitchell et al. | 156/252 |
| 5,653,473 | | 8/1997 | Laszutko et al. | 283/81 |
| 5,673,944 | * | 10/1997 | Walker et al. | 428/42.3 X |
| 5,752,722 | * | 5/1998 | Moore et al. | 428/42.2 X |
| 5,958,536 | * | 9/1999 | Gelsinger et al. | 428/40.1 |
| 5,966,852 | * | 10/1999 | Drzewiecki | 40/360 |

* cited by examiner

*Primary Examiner*—Daniel Zirker
(74) *Attorney, Agent, or Firm*—Oppenheimer Wolff & Donnelly LLP

(57) ABSTRACT

A multilayer index tab label insert sheet assembly with removable tab label inserts. An exemplary label insert sheet includes a face stock having a plurality of foldable tab label inserts, a release coated backing sheet generally coextensive with the face stock sheet, a pressure sensitive adhesive coating between the face stock sheet and the release coated backing sheet to secure those sheets together, and a patterned varnish coating underneath the index tab label inserts to allow the label inserts to be readily removed from the release coated backing sheet.

30 Claims, 2 Drawing Sheets

INDEX TAB LABEL INSERT SHEETS

FIELD OF THE INVENTION

The present invention relates to multilayer label assemblies, and more particularly, to an improved index tab label insert sheet that includes tab label inserts which may be printed on with identification indicia and inserted into transparent tabs of an index divider to help users identify the divider.

BACKGROUND OF THE INVENTION

Index divider sheets with transparent index tabs are articles used, for example, by school children, businessmen, and office workers. Users have employed index divider sheets to divide notebooks according to school subjects, reports according to chapters, and presentations according to sections, as well as for any other use where a collection of materials must be divided into sections that can be easily identified and accessed.

Concerning removable multilayer label assemblies which have been used, U.S. Pat. No. 4,910,058, issued to Jameson et al., discloses a multi-ply form with labels. The Jameson multi-ply form includes first and second carrier webs secured to each other by repositionable adhesive. Various labels are attached to die-cut portions of the second carrier web with a permanent adhesive. To use the multi-ply form with attached labels, the form is first disposed in a printer such that the necessary indicia may be preprinted on each of the labels. When removed from the printer, the first carrier web of the form may be removed from the second web, exposing the repositionable adhesive on the underside of the die-cut portions of the second web. The removed label may then be secured to a new surface using repositionable adhesive. The Jameson multi-ply form has three layers: (1) the first carrier web, (2) the second carrier web, and (3) a layer of labels. The number of layers in a multi-ply form or sheet directly affects its manufacturing costs. A multi-ply form with more layers requires more efforts to assemble and manufacture since it has more components, thereby costing more.

U.S. Pat. No. 5,135,261, issued to Cusack et al. (hereafter Cusack), discloses an index tab label assembly using a label having a coating that facilitates printing on the label. The Cusack label assembly has only two layers: (1) a backing sheet, and (2) a layer of removable labels. Each label is made out of a polyester film having a coating applied to the front side of the sheet to facilitate printing when using laser or xerographic equipment and a pressure-sensitive adhesive attached to the back side of the film. The labels may be releasably attached to a backing sheet. When so configured, the labels may be fed through laser or other printing equipment so that indicia such as numbers, letters, designs, may be printed on the labels. After indicia is printed on a label, the label may then be peeled from the backing sheet due to a release coating. The label may then be attached to a tab reinforcer using the pressure-sensitive adhesive that is applied on the back of the label. The tab reinforcer is then attached to a tab of the divider sheet. It is noted that when the user assembles and uses the Cusack index tab label assembly as disclosed, the divider may only be identified from one side since the identification indicia on the label can be read only from one side. In addition, the Cusack tab label has pressure sensitive adhesive thereon, making it more difficult to re-use the divider. BRIEF SUMMARY OF THE INVENTION The present invention pertains to the construction and use of a new and improved multilayer label assembly, and, in particular, to the construction and use of an index tab label insert sheet that (1) is cost-effective to manufacture, (2) has a dry peel feature, (3) can be passed through a printer or photocopier multiple times, and (4) has foldable tab label inserts which can be read and identified from both sides. An index tab label insert sheet in accordance with one exemplary embodiment of the present inventions includes, among other elements, (1) a face stock sheet having a plurality of foldable tab label inserts, (2) a backing sheet, preferably release coated, generally coextensive with the face stock sheet, (3) an adhesive coating, preferably a pressure sensitive adhesive coating, between the face stock sheet and the release coated backing sheet, and (4) a patterned varnish coating underneath the index tab label inserts, making the inserts readily removed from the release coated backing sheet.

The present invention increases manufacturing cost-effectiveness by having only two sheets: (1) a face stock sheet, and (2) a released coated backing sheet. By having only two sheets, the current novel tab label insert sheet assembly uses a minimal number of components and thereby requires less efforts to assemble. Therefore, production costs may be kept to a minimum.

Another unique feature of the present tab label insert sheet is its dry peel feature. A pressure sensitive adhesive coating is applied to the underside of the face stock sheet to secure the face stock sheet to the release coated backing sheet. A patterned varnish coating is applied to the underside of the removable tab label inserts on the face stock sheet. The patterned varnish coating facilitates the easy removal of the tab label inserts from the release coated backing sheet by deadening or reducing the stickiness of the adhesive. Furthermore, the varnish coating sufficient reduces the stickiness of the tab label inserts so that the removed inserts do not stick to the user's fingers and thereby avoid aggravating the user.

Another advantage of the present novel tab label insert sheet is its multi-pass capability. First, the low-tack design of the insert sheet allows for multi-pass capability. Adhesive bleeding is a condition where adhesive on a typical multilayer sheet is transferred from the sheet to internal parts of a printer or photocopier. The transferring effect is caused by the pressure and heat generated by the printer or photocopier as the typical multilayer sheet travels through the printer or photocopier. The current novel tab label insert sheet has a low-tack design where just enough, and not excessive, adhesive is applied to the sheet to secure the label inserts. Thus the low-tack design reduces the risk of adhesive bleeding commonly found with other self-adhesive label products; and means that even with repeated exposure to the heat and pressure of copier and printer rolls that adhesive bleed will not occur. Second, the inventive tab label insert sheet is sufficiently flexible and resilient so that it can be passed through a printer or photocopier multiple times. As a result, users may initially pass the inventive insert sheet through a printer to print indicia on a few of the label inserts, and may pass the sheet through the printer a second or third time to print indicia on a few other label inserts without having to discard the unused portion, thereby avoiding waste.

The above described and many other features and attendant advantages of the present invention will become apparent as the invention becomes better understood by reference to the following detailed description when considered in conjunction with the accompanying drawings.

DETAILED DESCRIPTION OF PREFERRED EMBODIMENT

The present invention pertains to the construction and use of a new and improved multilayer label assembly, and, in particular, to the construction and use of an index tab label insert sheet (1) that is cost-effective to manufacture, (2) that is relatively non-stick, (3) that can be passed through a printer or photocopier multiple times, and (4) that has foldable tab label inserts. The following detailed description is provided to enable any person skilled in the art to make and use the invention and to set forth the best modes contemplated by the inventor for carrying out the invention. This description is not to be taken in a limiting sense, but is made merely for the purpose of illustrating the general principles of the invention.

Figure 1:
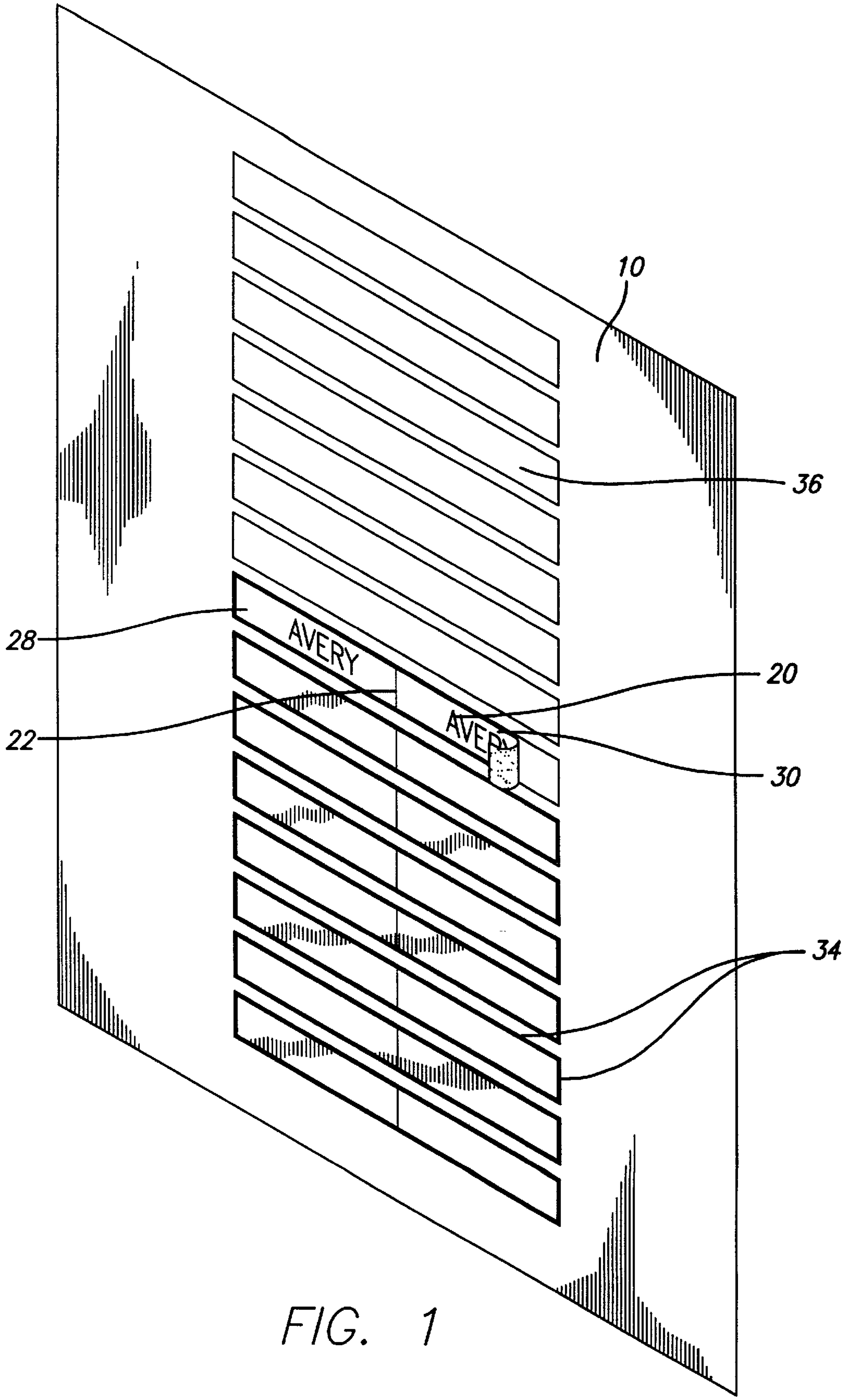
FIG. 1 is a perspective view of an exemplary index tab label sheet in accordance with the present invention.

As illustrated in FIG. 1, the index tab label inserts 20 are provided in transversely extending rows on an exemplary index tab label insert sheet 10. The exemplary insert sheet 10 in FIG. 1 illustrates fifteen index tab label inserts 20 in fifteen transversely extending rows; each row comprises one tab label insert 20. In practice, an insert sheet may include at least ten label inserts 20. FIG. 1 shows a number of empty rows 36 where corresponding tab label inserts have been removed. There is a die cut outline 34 encompassing the configuration of each tab label insert 20 to ease the removal of the insert 20 from the insert sheet 10.

Figure 3:
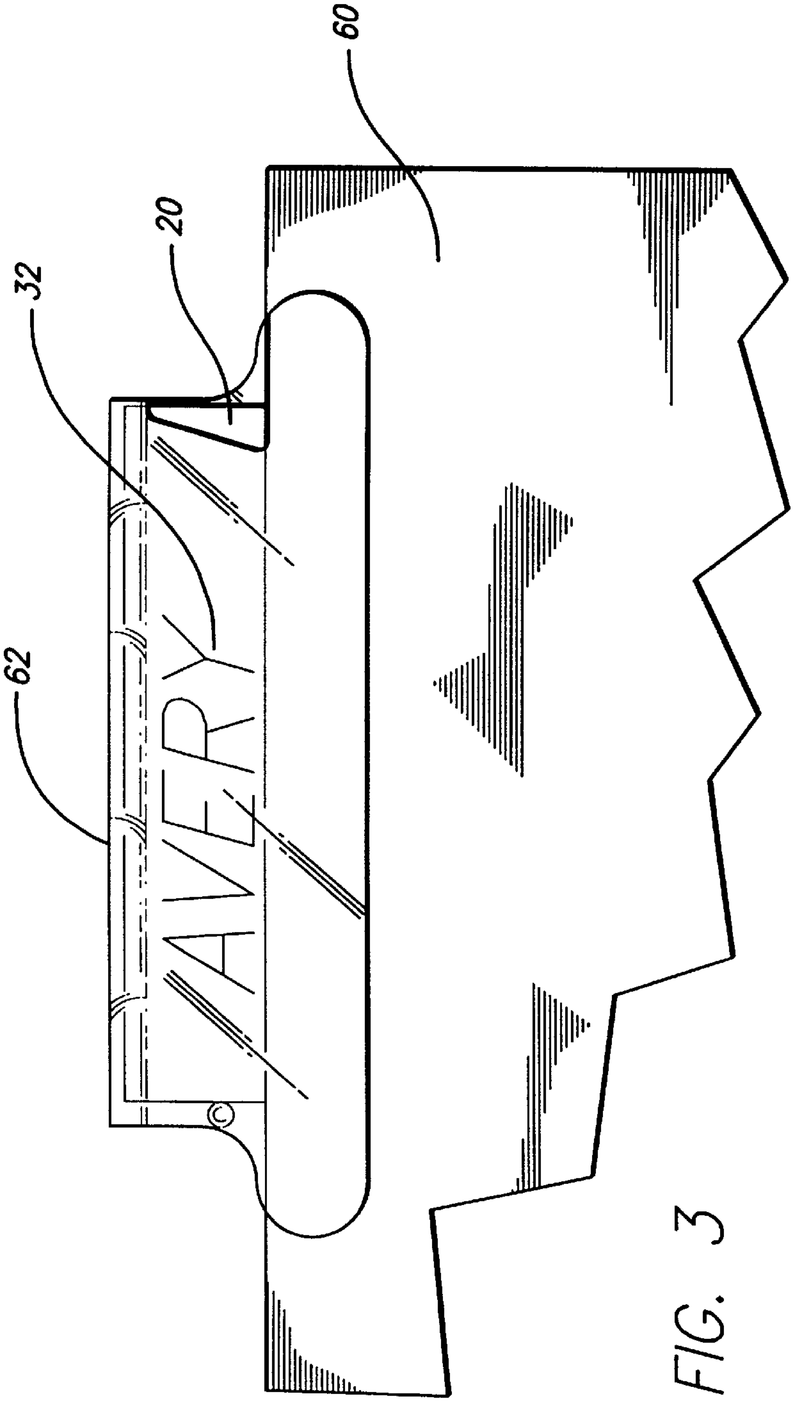
FIG. 3 shows a partial top view of a tab label insert of the present invention inserted in the transparent tab index of an index divider.

Each tab label insert 20 has a center fold line 22. The center fold line 22 divides each tab label insert 20 into a left printable half 28 and a right printable half 30. One tab label insert 20 is shown with identical indicia 32 printed on both printable halves 28,30. The center fold line 22 is also a line of weakness designed to facilitate the folding of each tab label insert 20 in halves. The line of weakness may be realized by perforations, or by die cutting part way through the face stock, or in any other desired way. FIG. 3 shows a folded tab label insert 20 with the desired indicia 32 inserted in the transparent tab 62 of an index divider 60. The insertion is done such that the sides of the tab label insert 20 bearing the printed indicia face outwardly.

To use a multilayer index tab label inserts sheet 10, a user initially sends the sheet 10 through a printer or copier to print desired indicia on one or more tab label inserts 20 on the sheet 10. A user may print identical indicia 32 on each half 28,30 of a tab label insert 20. The user may then remove the printed tab label insert 20 from the tab label insert sheet 10 along the die cut outlines 34, fold the insert 20 along its center fold line 22, and place the folded insert 20 inside the transparent tab 62 of an index divider 60 with the sides containing the printed indicia facing outwardly, as shown in FIG. 3. When the user prints identical indicia on each printable half 28, 30 of a tab label insert 20 and places the printed label insert 20 inside the transparent tab 62 of an index divider 60 as described above, the index divider can be identified by looking at either side of the divider's transparent tab 62.

The user can send the current novel tab label insert sheet 10 through a printer or photocopier multiple times. First, the low-tack design of the insert sheet 10 allows for multi-pass capability. Adhesive bleeding is a condition where adhesive on a typical multilayer sheet is transferred from the sheet to internal parts of a printer or photocopier. The transferring effect is caused by the pressure and heat generated by the printer or photocopier as the typical multilayer sheet travels through the printer or photocopier. The current novel tab label insert sheet 10 has a low-tack design where just enough, and not excessive, adhesive is applied to the sheet 10 to secure the label inserts 20. Thus the low-tack design reduces the risk of adhesive bleeding commonly found in other self-adhesive label products. Second, the inventive tab label insert sheet 10 is sufficiently flexible and resilient so that it can be passed through a printer or photocopier multiple times. As a result, the user may print and use a few of the label inserts 20 at one time and economically save the unused portion of the label insert sheet 10 for use at another time.

Figure 2:
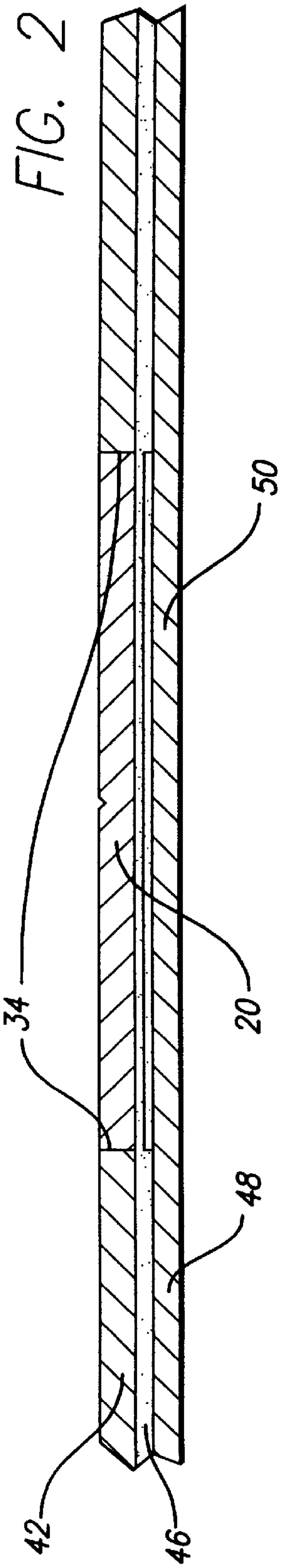
FIG. 2 illustrates a cross-sectional view of the index tab label sheet taken along line 2—2 of FIG. 1.

FIG. 2 illustrates a cross-sectional view of an exemplary index tab label insert sheet 10. The face stock sheet 42 is the top layer of the insert sheet 10. A pressure sensitive adhesive coating 46 is applied to the underlying surface of the face stock sheet 42. The pressure sensitive adhesive coating 46 secures the face stock sheet 42 to the release coated backing sheet 48. A patterned varnish coating 50 is applied underneath each tab label index 20 between the pressure sensitive adhesive coating 46 and the release coated backing sheet 48, and in practice may be applied in a patterned way to the backing sheet 48 in areas where the labels are located.

An exemplary tab label insert sheet 10 has a preferred thickness of approximately 8 to 12.5 mils with the face stock sheet 42 being approximately 5 to 8 mils thick, the release coated backing sheet 48 being approximately 2 to 3 mils thick, and the pressure sensitive adhesive coating 46 and the patterned varnish coating 50 together being approximately 1 to 1.5 mils thick. More generally the tab label index sheets 10 could be from about 8 mils to about 12 or 15 mils thick, in order to reliably feed through printer or copier machines. It is further noted that the face stock sheet 42 is normally substantially thicker than the backing sheet 48, and may be 2 or 3 times as thick as the backing sheet 48.

The patterned varnish coating 50 deadens or reduces the stickiness of the adhesive. Thus a user can readily remove a tab label insert 20 from the release coated backing sheet 48 along the die cut outlines 34 encompassing the configuration of the label insert 20. Furthermore, the die cut outlines 34 sufficiently penetrate the face stock sheet 42 and the pressure sensitive adhesive coating 46 such that when a tab label insert 20 is removed, the pressure sensitive adhesive and the varnish underneath the label insert 20 remains with the insert 20. The varnish coating 50 prevents the removed tab label insert 20 from sticking to the fingers of the user and thereby prevents the user from getting aggravated. Also, when the user folds the tab label insert 20 in halves, the varnish coating 50 also prevents the halves from sticking together in case an erroneous initial folding is done.

In the preferred embodiment, the face stock sheet 42 used is Champion's 80# Pinehurst available from Rollsource at 2392 South Wolf Road. Des Plaines, Ill. 60018. The notation "#" is a term of art representing the weight of a particular type of paper measured in a standard manner, in pounds. For example, "80#" means that 500 sheets of Champion's Pinehurst 80# Pinehurst face stock, having the dimensions of 25 inches by 38 inches per sheet, would weigh 80 pounds. This 80 pound paper is about 5.8 to 6.1 mils thick. The backing sheet is 42# Super Calendared Liner available from Avery Engineering Coating Division, and is about 2.5 mils thick. The address for Avery Engineering Coating Division is 7070 Spinach Drive, Mentor, Ohio. 44060. The preferred adhesive is P-39 available from Avery Central Products Division, and the preferred varnish is a gloss coating available from Sun Chemical, as formula number RCA01291. The address for Avery Central Products Division is 4350 Avery Drive, P.O. Box 547, Flowery Branch, Ga. 30542. Sun Chemical's address is 795 Beahan Rose, Rochester, N.Y. 14621. It should be noted that the above-described face stock sheet, backing sheet, adhesive, and varnish are used in the preferred embodiment. However, other types of face stock, backing sheet, as well as adhesive and varnish, may be employed.

Although the present invention has been described in terms of the preferred embodiment above, numerous modifications and/or additions to the above-described preferred embodiment would be readily apparent to one skilled in the art. Thus, by way of example and not of limitation, each row of tab label insert may comprise of more than one label insert 20. Also, the preferred embodiment in FIG. 1 having fifteen index tab label inserts 20. However, an alternative embodiment of the current tab label insert sheet 10 may contain at least ten inserts 20. Furthermore, in the exemplary embodiment, the tab label insert sheet 10 is 8 to 12.5 mils in thickness with the face stock sheet 42 being approximately 5 to 8 mils thick, the release coated backing sheet 48 being approximately 2 to 3 mils thick, and the pressure sensitive adhesive coating 46 and the patterned varnish coating 50 together being approximately 1 to 1.5 mils thick. However, a thicker release coated backing sheet 48 or face stock sheet 42, or a thicker pressure sensitive adhesive coating 46 or patterned varnish coating 50 may be used. Also, the backing sheet 48 need not be provided with the usual silicone release coating, as the varnish in the label insert areas would still permit removal of the label inserts 20. However the use of a release coated backing sheet and a fairly aggressive adhesive is preferred. It is further noted that other dry-peel materials, such as paint, for specific example, could be employed instead of varnish to provide initial adhesion, but no stickiness following peeling off of the label inserts. Accordingly, the present invention is not limited to the specific embodiment illustrated and described hereinabove.

What is claimed is:

1. A multilayer sheet assembly, comprising:

a face stock sheet, having a printable surface and an underside surface;

said face stock sheet having a plurality of tab label inserts; each tab label insert having a center fold line dividing the label insert into a first printable half and a second printable half; said center fold line being a line of weakness to facilitate the folding of the tab label insert in half;

said face stock sheet has a plurality of die cut outlines; each die cut outline encompassing the configuration of one tab label insert;

a release coated backing sheet generally coextensive with said face stock sheet;

a pressure sensitive adhesive coating between said face stock sheet and said release coated backing sheet;

a patterned varnish coating underneath said index tab label inserts between said pressure sensitive adhesive coating and said release coated backing sheet; said patterned varnish coating allowing said tab label inserts to be readily removed from said release coated backing sheet; and said multilayer sheet assembly being sufficiently flexible and resilient to reliably pass through a printer multiple times, and being approximately 8 to 8.5 mils in thickness;

whereby said tab label inserts may be initially printed on with desired writing, removed from the multilayer sheet, and folded along said center fold line for insertion into a transparent index tab of an index divider.

2. A multilayer sheet assembly as claimed in claim 1, wherein said face stock sheet is approximately 4 mils in thickness, said release coated backing sheet is approximately 3 mils in thickness, and said pressure sensitive adhesive coating and said patterned varnish coating together are approximately 1 to 1.5 mils in thickness.

3. A multilayer sheet assembly as claimed in claim 1, wherein said patterned dry peel coating is a gloss varnish coating.

4. A multilayer sheet assembly as claimed in claim 3, wherein said adhesive is sufficiently aggressive that the unused label inserts are held in position despite repeated passes of said sheet assembly through a printer or copier in the printing of successive inserts.

5. A multilayer sheet assembly as claimed in claim 3, wherein said face stock sheet includes at least ten of said label inserts.

6. A multilayer sheet assembly as claimed in claim 1 wherein the varnish is affixed to the label via the adhesive coating with the label removed from thc backing sheet.

7. A method for labeling a transparent tab of an index divider, comprising:

printing a desired indicia on a multilayer sheet assembly; said multilayer sheet assembly including:

(a) a face stock sheet having a plurality of tab label inserts; each index tab label having a center fold line;

(b) a release coated backing sheet generally coextensive with said face stock sheet;

(c) a pressure sensitive adhesive coating between said face stock sheet and said release coated backing sheet;

(d) a patterned varnish coating underneath said index tab label inserts between said pressure sensitive adhesive coating and said release coated backing sheet; said patterned varnish coating allowing said index tab label inserts to be readily removable from said multilayer sheet assembly;

removing said tab label inserts from said multilayer sheet assembly, folding said tab label inserts along said center fold line; and inserting each said tab label insert into a transparent index tab of an index divider so that said desired indicia faces outwardly.

8. A method for labeling a transparent tab of an index divider as claimed in claim 7, including a step of forming said multilayer sheet assembly using said face stock sheet, said release coated backing sheet, said pressure sensitive adhesive coating, and said patterned varnish coating, such that said sheet assembly is no more than 15 mils in thickness.

9. A method for labeling a transparent tab of an index divider as claimed in claim 7, including a step of forming said multilayer sheet assembly using said face stock sheet and said release coated backing sheet, wherein said face stock sheet is substantially thicker than said release coated backing sheet and said assembly is no more than 12 mils thick.

10. A method for labeling a transparent tab of an index divider as claimed in claim 7, including a step of forming said center fold line as a line of weakness.

11. A method for labeling a transparent tab of an index divider as claimed in claim 7, including the steps of printing on some but not all of said label inserts; removing and utilizing said printed label inserts; subsequently printing on additional label inserts on the same sheet; and then removing and utilizing these additional printed label inserts.

12. A method for labeling a transparent tab of an index divider as claimed in claim 7, including the step of forming a plurality of die cut outlines on said face stock sheet wherein each of said die cut outlines encompasses the configuration of one tab label insert.

13. A method for labeling a transparent tab of an index divider as claimed in claim 7, including a step of forming wherein said patterned varnish coating is a gloss coating.

14. A method for labeling a transparent tab of an index divider as claimed in claim 7, including a step of forming said multilayer sheet assembly using a pressure sensitive adhesive coating and a varnish coating together being approximately 1.0 to 1.5 mils in thickness.

15. A method for labeling a transparent tab of an index divider as claimed in claim 7, including a step of forming said die cut outlines wherein said outlines are sufficiently deep so that when said tab label insert is removed the pressure sensitive adhesive and varnish coatings underneath said tab label insert remain with said tab label insert.

16. A method for labeling a transparent tab of an index divider as claimed in claim 7, wherein the patterned varnish is affixed to the label via the adhesive coating with the label removed from the backing sheet.

17. A method for labeling a transparent tab of an index divider as claimed in claim 16, wherein the tab label inserts are substantially nonstick due to the varnish.

18. A method for labeling a transparent tab of an index divider as claimed in claim 7 further comprising printing on one side of the index tab label, said side of the label not communicating with the varnish.

19. A method for labeling a transparent tab of an index divider, comprising:

printing a desired indicia on a multilayer sheet assembly; said multilayer sheet assembly including:

(a) a face stock sheet having a plurality of tab label inserts; each index tab label having a center fold line;

(b) a release coated backing sheet generally coextensive with said face stock sheet;

(c) a pressure sensitive adhesive coating between said face stock sheet and said release coated backing sheet;

(d) a patterned coating underneath said index tab label inserts between said pressure sensitive adhesive coating and said release coated backing sheet; said patterned coating allowing said index tab label inserts to be readily removable from said multilayer sheet assembly;

removing said tab label inserts from said multilayer sheet assembly;

folding said tab label inserts along said center fold line; and inserting each said tab label insert into a transparent index tab of an index divider so that said desired indicia faces outwardly.

20. A method for labeling a transparent tab of an index divider as claimed in claim 19, wherein the patterned coating is affixed to the label via the adhesive coating with the label removed from the backing sheet.

21. A method for labeling a transparent tab of an index divider as claimed in claim 20, wherein the tab label inserts are substantially nonstick due to the coating.

22. A method for labeling a transparent tab of an index divider as claimed in claim 19 further comprising printing on one side of the index tab label, said side of the label not communicating with the coating.

23. A multilayer sheet assembly for multiple feedings through a printer without adhesive bleeding, the assembly comprising:

a face stock sheet having a printable surface and an underside surface;

said face stock sheet having a plurality of tab label inserts; each tab label insert having a center fold line dividing the label insert into a first printable half and a second printable half; said center fold line being a line of weakness to facilitate the folding of the tab label insert in half, a release coated backing sheet generally coextensive with said face stock sheet;

a pressure sensitive adhesive coating between said face stock sheet and said release coated backing sheet; and a patterned varnish coating underneath said index tab label inserts between said pressure sensitive adhesive coating and said release coated backing sheet; said patterned varnish reducing adhesive bleeding into a printer when the face stock sheet is passed through the printer for a printing operation on the tab label inserts.

24. A multilayer sheet assembly as claimed in claim 23, wherein said face stock sheet is approximately 4 mils in thickness, said release coated backing sheet is approximately 3 mils in thickness, and said pressure sensitive adhesive coating and said patterned varnish coating together are approximately 1 to 1.5 mils in thickness.

25. A multilayer sheet assembly as claimed in claim 23, wherein said patterned varnish is a gloss varnish coating.

26. A multilayer sheet assembly as claimed in claim 25, wherein said adhesive is sufficiently aggressive that the unused label inserts are held in position despite repeated passes of said sheet assembly through a printer or copier in the printing of successive inserts.

27. A multilayer sheet assembly as claimed in claim 25, wherein said face stock sheet includes at least ten of said label inserts.

28. A multilayer sheet assembly as claimed in claim 23, wherein the patterned coating is affixed to the label via the adhesive coating with the label removed from the backing sheet.

29. A multilayer sheet assembly as claimed in claim 28, wherein the tab label inserts are substantially nonstick due to the coating.

30. A multilayer sheet assembly as claimed in claim 23, wherein the printing is done on one side of the index tab label, said side of the label not communicating with the coating.

* * * * *